United States Patent
Oda

(10) Patent No.: US 10,497,468 B2
(45) Date of Patent: Dec. 3, 2019

(54) CLINICAL LABORATORY TEST APPARATUS AND SYSTEM

(71) Applicant: FUJIFILM Corporation, Tokyo (JP)

(72) Inventor: Yoshinari Oda, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/127,253

(22) Filed: Sep. 11, 2018

(65) Prior Publication Data

US 2019/0080786 A1    Mar. 14, 2019

(30) Foreign Application Priority Data

Sep. 12, 2017    (JP) .................................. 2017-174907

(51) Int. Cl.
    *G06F 17/00*    (2019.01)
    *G16H 10/40*    (2018.01)
    (Continued)

(52) U.S. Cl.
    CPC ............ *G16H 10/40* (2018.01); *B01L 3/5453* (2013.01); *G01N 35/00732* (2013.01);
    (Continued)

(58) Field of Classification Search
    CPC ............. B01L 2300/021; B01L 3/5453; G01N 2035/00752; G01N 35/00732; G06K 19/06028; G06K 7/10861; G16H 10/40
    See application file for complete search history.

(56) References Cited

U.S. PATENT DOCUMENTS 5,281,395 A  * 1/1994   Markart ............. G01N 21/8483
                                                   235/375
5,688,361 A  * 11/1997  Itoh ....................... B01L 3/5453
                                                   156/352

(Continued)

FOREIGN PATENT DOCUMENTS

EP    2020639    2/2009
EP    2277624    1/2011

(Continued)

OTHER PUBLICATIONS

"Search Report of Europe Counterpart Application", dated Nov. 20, 2018, p. 1-p. 6.

(Continued)

*Primary Examiner* — Thien M Le
(74) *Attorney, Agent, or Firm* — JCIPRNET

(57) ABSTRACT

A clinical laboratory test apparatus of a health care information system includes a reading section that reads an optically readable code array, an extraction section that extracts, from a plurality of the code arrays read by the reading section, a rule that is common between the plurality of code arrays, a storage section that stores the rule extracted by the extraction section, and a determination section that determines authenticity of each of the code arrays read by the reading section based on the rule stored in the storage section. In testing a sample, in a case where it is determined by the determination section that the code array read by the reading section is true, the test is executed, and in a case where it is determined that the code array is false, the execution of the test is suspended.

19 Claims, 7 Drawing Sheets

(51) Int. Cl.
*B01L 3/00* (2006.01)
*G01N 35/00* (2006.01)
*G06K 7/10* (2006.01)

(52) U.S. Cl.
CPC .... *G06K 7/10861* (2013.01); *B01L 2300/021* (2013.01); *G01N 2035/00752* (2013.01)

(56) References Cited

U.S. PATENT DOCUMENTS

| | | | |
|---|---|---|---|
| 2001/0024095 A1* | 9/2001 | Fitzgibbon | E05D 15/38 318/480 |
| 2002/0111741 A1 | 8/2002 | Abraham-Fuchs et al. | |
| 2005/0064435 A1* | 3/2005 | Su | B82Y 5/00 435/6.11 |
| 2011/0045521 A1* | 2/2011 | Itoh | G01N 35/04 435/29 |
| 2017/0185815 A1* | 6/2017 | Itoh | G06K 7/1413 |

FOREIGN PATENT DOCUMENTS

| | | |
|---|---|---|
| EP | 3115961 | 1/2017 |
| JP | 2007226834 | 9/2007 |

OTHER PUBLICATIONS

"Office Action of Europe Counterpart Application", dated Aug. 23, 2019, p. 1-p. 3.

* cited by examiner

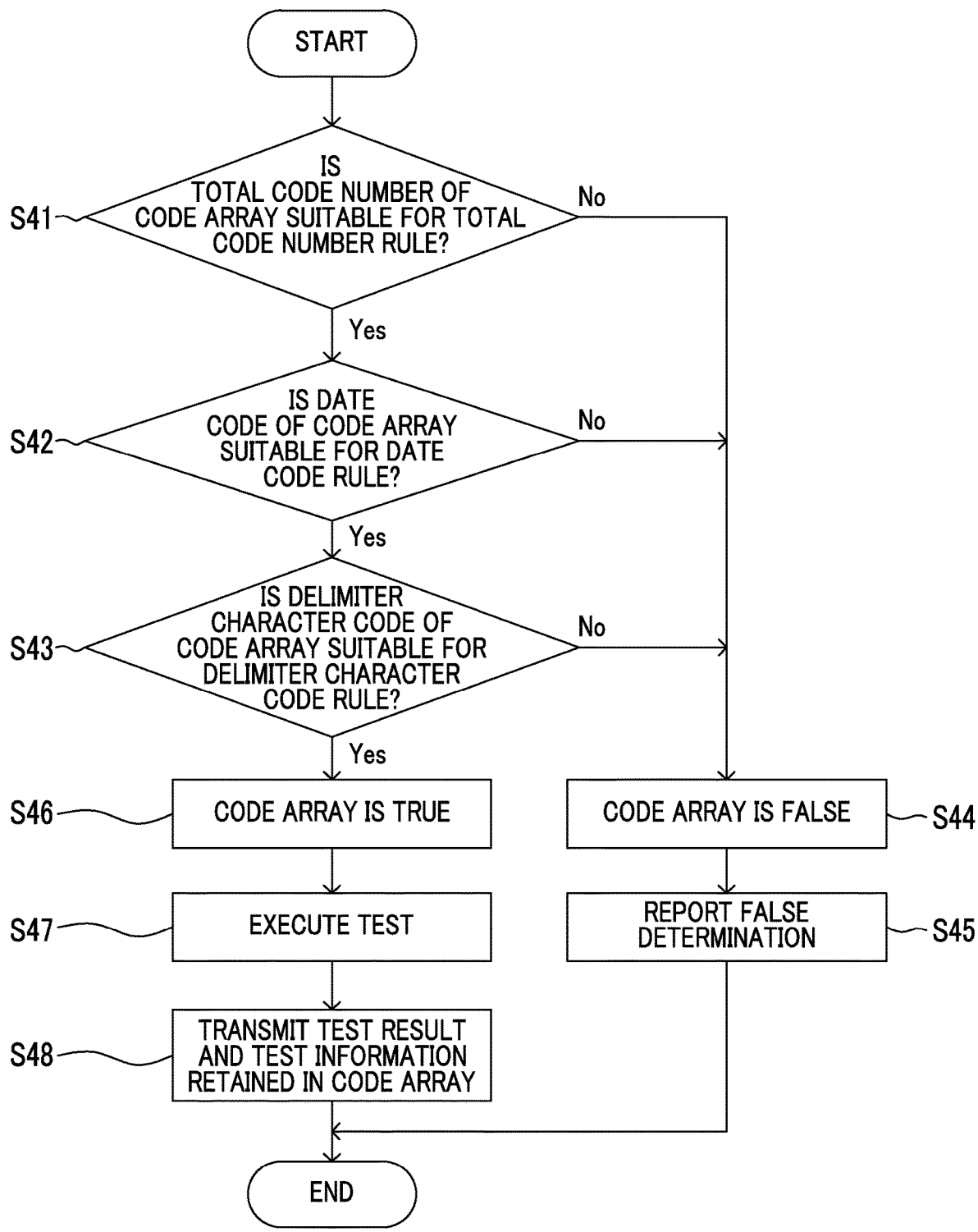

CLINICAL LABORATORY TEST APPARATUS AND SYSTEM

CROSS-REFERENCE TO RELATED APPLICATIONS

This application claims the benefit of Japanese Patent Application JP 2017-174907, filed Sep. 12, 2017, the entire content of which is hereby incorporated by reference, the same as if set forth at length.

BACKGROUND OF THE INVENTION

1. Field of the Invention

The present invention relates to a clinical laboratory test apparatus and system.

2. Description of the Related Art

A health care organization such as a hospital uses a medical information system that manages a test order and a test result for a clinical laboratory test performed in the health care organization. A barcode is given to a sample container that contains a sample (for example, blood, viscous liquid, or the like) gathered for the clinical laboratory test, and test information (for example, a test subject identification (ID), a test date, a test type, or the like) for specifying the test order is retained in the barcode.

In the clinical laboratory test apparatus, the barcode of the sample container is read, and the test information retained in the barcode and a test result are associated with each other. Further, the associated test information and test result are transmitted to a server of the medical information system from the clinical laboratory test apparatus. The server stores the input test information and manages the progress of the test order on the basis of the input test information (for example, see JP2007-226834A).

SUMMARY OF THE INVENTION

In a case where dirt, dust, or the like is attached to the barcode of the sample container, there is a concern that the barcode is read erroneously by the clinical laboratory test apparatus. Further, since barcodes are given to various products, there is also a concern that a barcode that is not related to the barcode used in the clinical laboratory test is read by the clinical laboratory test apparatus. In these cases, a test result may be input to the server in association with the erroneously read test information.

The erroneously read test information does not match any test order managed by the server, and thus, it is necessary to perform matching, through a manual operation, between the test result and the test order that are associated with the erroneously read test information, which imposes a burden on a manager of the system. Further, a medical care for a test subject is delayed until the matching is completed. In addition, in a case where even the matching through the manual operation is unavailable, re-test is necessary, which also imposes a burden on the test subject.

In a case where a list of the test orders is transmitted to the clinical laboratory test apparatus from the server and the clinical laboratory test apparatus reads the barcode, if the clinical laboratory test apparatus is configured to search for a test order that matches test information retained in the barcode from the list, it is possible to find out mistaken reading of the barcode before execution of the test, and to solve the problem of imposing a burden on the manager of the system and the test subject.

However, a configuration in which the list of the test orders is transmitted to the clinical laboratory test apparatus from the server needs bi-directional communication between the clinical laboratory test apparatus and the server, which may lead to complication of the system. Further, in a case where the clinical laboratory test apparatus cannot acquire the list of the test orders due to communication interference or the like, it causes a hindrance in execution of the test.

The invention has been made in consideration of the above-mentioned problems, and an object of the invention is to provide a clinical laboratory test apparatus and system capable of determining authenticity of an optically readable code array such as a barcode read by the clinical laboratory test apparatus in a clinical laboratory test, using only the clinical laboratory test apparatus before execution of the test, and allowing smooth management of the system that includes the clinical laboratory test apparatus.

A clinical laboratory test apparatus according to an aspect of the invention comprises: a reading section that reads an optically readable code array; an extraction section that extracts, from a plurality of the code arrays read by the reading section, a rule that is common between the plurality of code arrays; a storage section that stores the rule extracted by the extraction section; and a determination section that determines authenticity of each of the code arrays read by the reading section on the basis of the rule stored in the storage section, in which the rule includes a total code number of the code array, the determination section determines that the code array is true in a case where a total code number of the code array read by the reading section matches the total code number of the rule, and determines that the code array is false in a case where the total code number of the code array read by the reading section does not match the total code number of the rule, and in testing a sample, in a case where it is determined by the determination section that the code array read by the reading section is true, the test is executed, and in a case where it is determined that the code array is false, the execution of the test is suspended.

Further, a clinical laboratory test apparatus according to an aspect of the invention comprises: a reading section that reads an optically readable code array; an extraction section that extracts, from a plurality of the code arrays read by the reading section, a rule that is common between the plurality of code arrays; a storage section that stores the rule extracted by the extraction section; and a determination section that determines authenticity of each of the code arrays read by the reading section on the basis of the rule stored in the storage section, in which the rule includes a format of date codes included in the code array and positions thereof in the code array, the determination section determines that the code array is true in a case where a format and positions of the date codes of the code array read by the reading section match the format and the positions of the date codes of the rule, and determines that the code array is false in a case where the format and the positions of the date codes of the code array read by the reading section do not match the format and the positions of the date codes of the rule, and in testing a sample, in a case where it is determined by the determination section that the code array read by the reading section is true, the test is executed, and in a case where it is determined that the code array is false, the execution of the test is suspended.

In addition, a clinical laboratory test apparatus according to an aspect of the invention comprises: a reading section that reads an optically readable code array; an extraction section that extracts, from a plurality of the code arrays read by the reading section, a rule that is common between the plurality of code arrays; a storage section that stores the rule extracted by the extraction section; and a determination section that determines authenticity of each of the code arrays read by the reading section on the basis of the rule stored in the storage section, in which the rule includes a type of a delimiter character code included in the code array and a position thereof in the code array, the determination section determines that the code array is true in a case where a type and a position of the delimiter character code of the code array read by the reading section match the type and the position of the delimiter character code of the rule, and determines that the code array is false in a case where the type and the position of the delimiter character code of the code array read by the reading section do not match the type and the position of the delimiter character code of the rule, and in testing a sample, in a case where it is determined by the determination section that the code array read by the reading section is true, the test is executed, and in a case where it is determined that the code array is false, the execution of the test is suspended.

In addition, a system according to an aspect of the invention comprises: a server that manages a test order and a test result; and the clinical laboratory test apparatus, in which the code array determined to be true by the determination section includes a code array that retains test information for specifying the test order, and the clinical laboratory test apparatus transmits the code array determined to be true by the determination section in testing a sample and a test result obtained by the test to the server in association.

According to the invention, in a clinical laboratory test, it is possible to determine authenticity of an optically readable code array of a barcode or the like read by a clinical laboratory test apparatus only using the clinical laboratory test apparatus before execution of the test, and to smoothly operate a system including the clinical laboratory test apparatus.

BRIEF DESCRIPTION OF THE DRAWINGS

FIG. 7 is a flowchart of an example of a process in a case where a clinical laboratory test is performed, executed by the controller of the clinical laboratory test apparatus.

EXPLANATION OF REFERENCES

Figure 1:
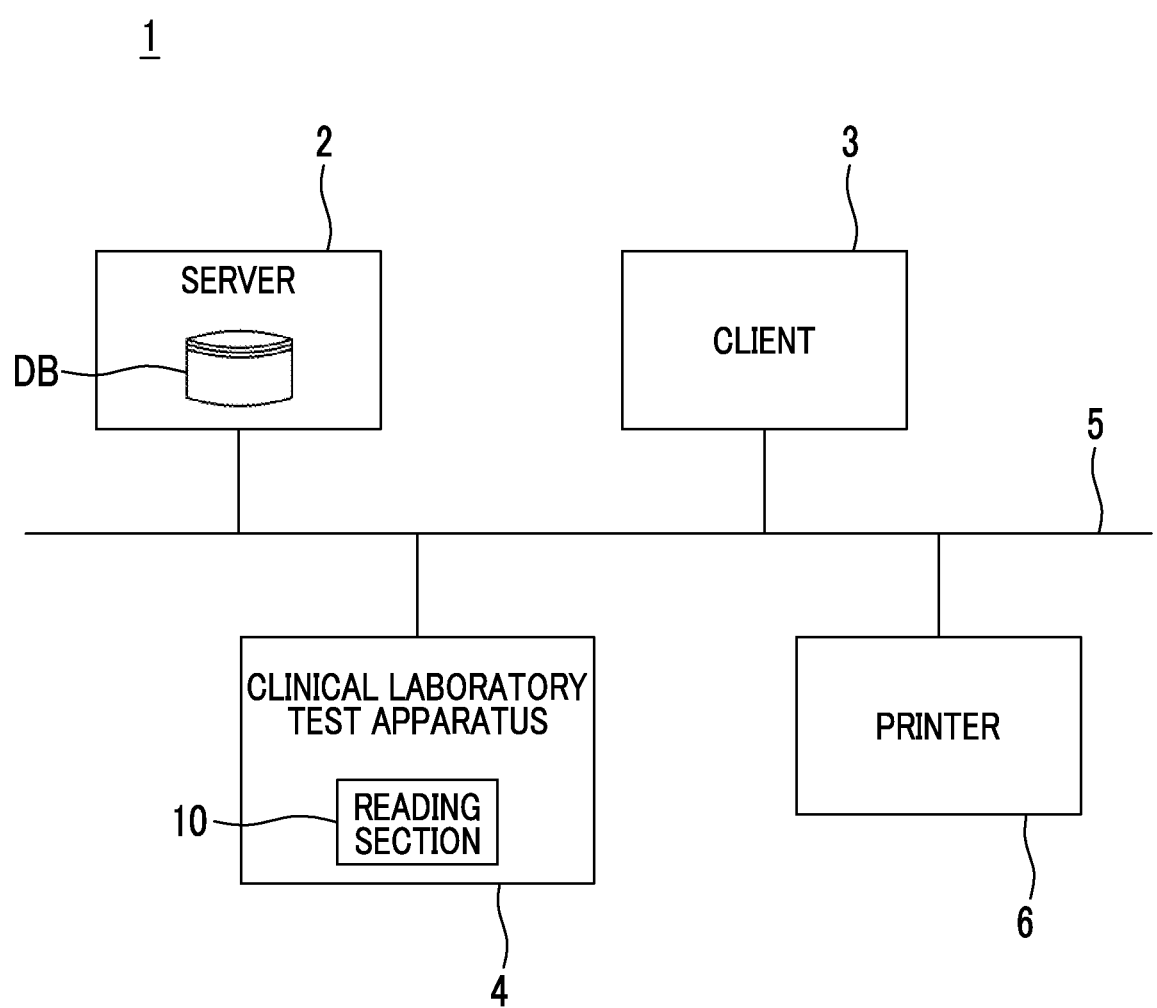
FIG. 1 is a schematic diagram of an example of a medical information system, for illustrating an embodiment of the invention.

1: medical information system
2: server
3: client
4: clinical laboratory test apparatus
5: network
6: printer
10: reading section
11: operating section
12: test section
13: report section
14: communication section
15: storage section
16: controller
17: display panel
18: extraction section
19: determination section
DB: database
St1: character string
St2: character string
St3: character string

DESCRIPTION OF THE PREFERRED EMBODIMENTS

FIG. 1 shows an example of a medical information system, for illustrating an embodiment of the invention.

A medical information system (hereinafter, simply referred to as a system) 1 is a system that is introduced to a health care organization such as a hospital and manages a test order and a test result of a clinical laboratory test performed in the health care organization. The clinical laboratory test means a test for analyzing components with respect to a sample such as blood, viscous liquid, or urine gathered from a test subject (for example, a patient) for detecting viruses or bacteria.

The system 1 includes a server 2, a client 3, and a clinical laboratory test apparatus 4. Here, the server 2, the client 3, and the clinical laboratory test apparatus 4 are connected to each other through a network 5 such as a local area network (LAN).

The server 2 is a computer that includes a processor such as a central processing unit (CPU), a memory such as a read only memory (ROM), a random access memory (RAM) or a hard disk drive (HDD), an input device such as a keyboard or a mouse, and a display device such as a cathode ray tube (CRT) or a liquid crystal display (LCD). As the processor is operated according to a program stored in the memory, the server 2 realizes a function for managing a test order and a test result of a clinical laboratory test.

The client 3 is a computer that includes a processor such as a central processing unit (CPU), a memory such as a read only memory (ROM), a random access memory (RAM) or a hard disk drive (HDD), an input device such as a keyboard or a mouse, and a display device such as a cathode ray tube (CRT) or a liquid crystal display (LCD). As the processor is operated according to a program stored in the memory, or as the processor is operated according to a program provided from the server 2 through the network 5, the client 3 realizes a function for issuing a test order.

The client 3 is provided in a medical examination room, for example, and is operated by a doctor. For example, in a case where the doctor determines that it is necessary to perform a clinical laboratory test with respect to a test subject, test information is input to the client 3 from the doctor. The test information includes, for example, a test subject identification (ID), a test date, a test type, or the like. The client 3 issues a test order on the basis of the input test information, and transmits the issued test order to the server 2.

The memory of the server 2 is provided with a database DB that stores a test order and a test result. The server 2 accepts a test order received from the client 3, and stores the accepted test order in the database DB. Further, the server 2 generates an optically readable code array on the basis of the test information (test subject ID, test date, test type, or the like) of the accepted test order.

The optically readable code array includes a one-dimensional code (so-called barcode) that retains information by a one-directional array pattern of two color lines (typically, black and white) having different reflective indexes and a two-dimensional code that retains information by a bi-directional array pattern of two color dots (typically, black and white) having different reflective indexes.

With respect to a test subject for which it is determined by a doctor that it is necessary to perform a clinical laboratory test, a sample according to the test is gathered for a clinical laboratory test room. A printer 6 is provided in the clinical laboratory test room. A code array generated by the server 2 is transmitted to the printer 6 from the server 2, and then, the printer 6 prints the received code array on a medium. The medium is a label, for example, and the label on which the code array is printed is attached to a sample container that contains the sample gathered from the test subject.

The clinical laboratory test apparatus 4 is provided in the clinical laboratory test room, and performs a test with respect to the sample contained in the sample container. The clinical laboratory test apparatus 4 is a blood analyzer that measures a red blood cell count, a white blood cell count, a blood platelet count, a hemoglobin concentration, and the like in blood, a urine analyzer that measures protein, glucose, occult blood, and the like in urine, and an immunochromatographic apparatus that measures antigens such as viruses in blood or viscous liquid using antigen-antibody reaction.

Here, a measurement principle of the immunochromatographic apparatus will be briefly described. A sample liquid (blood, viscous liquid, or the like) is dropped onto a chromatography test piece formed of a cellulose membrane or the like, the dropped sample liquid flows on the test piece due to a capillary phenomenon. In a portion of the test piece on which the sample liquid is dropped, labeled antibodies labeled by gold colloid particles are provided, and in a case where antigens are included in the sample liquid, the antigen and the labeled antibodies are combined with each other to form antigen-antibody composites. The antigen-antibody composites move on the flow of the sample liquid.

Further, on a downstream side of the test piece on which the sample liquid flows, a reaction part is provided, and captured antibodies to be combined with the antigens are fixedly provided in the reaction part. The antigen-antibody composites that move on the flow of the sample liquid are captured in the captured antibodies of the reaction part, and are fixed in the reaction part. As the antigen-antibody composites are fixed in the reaction part, the reaction part is colored by the gold colloid particles attached to the labeled antibodies of the antigen-antibody composites, and as the amount of the fixed antigen-antibody composites becomes larger, the coloring of the reaction part becomes stronger. The color presentation of the reaction part is optically detected as a change of absorbance, and the antigens in the sample liquid are measured.

The clinical laboratory test apparatus 4 includes a reading section 10 that reads the code array attached to the sample container, and acquires test information retained in the code array read by the reading section 10. Further, the clinical laboratory test apparatus 4 transmits the test information acquired from the code array attached to the sample container and a test result obtained by testing the sample contained in the sample container to the server 2 in association.

The server 2 stores the test result received from the clinical laboratory test apparatus 4 in the database DB, and manages the test result stored in the database DB using the test information (test subject ID, test date, test type, or the like) associated with the test result in a searchable manner. Further, the server 2 selects the test order corresponding to the received test information from test orders stored in the database DB, and changes a status of the selected test order from non-completion to completion to manage the progress of the test order.

Figure 2:
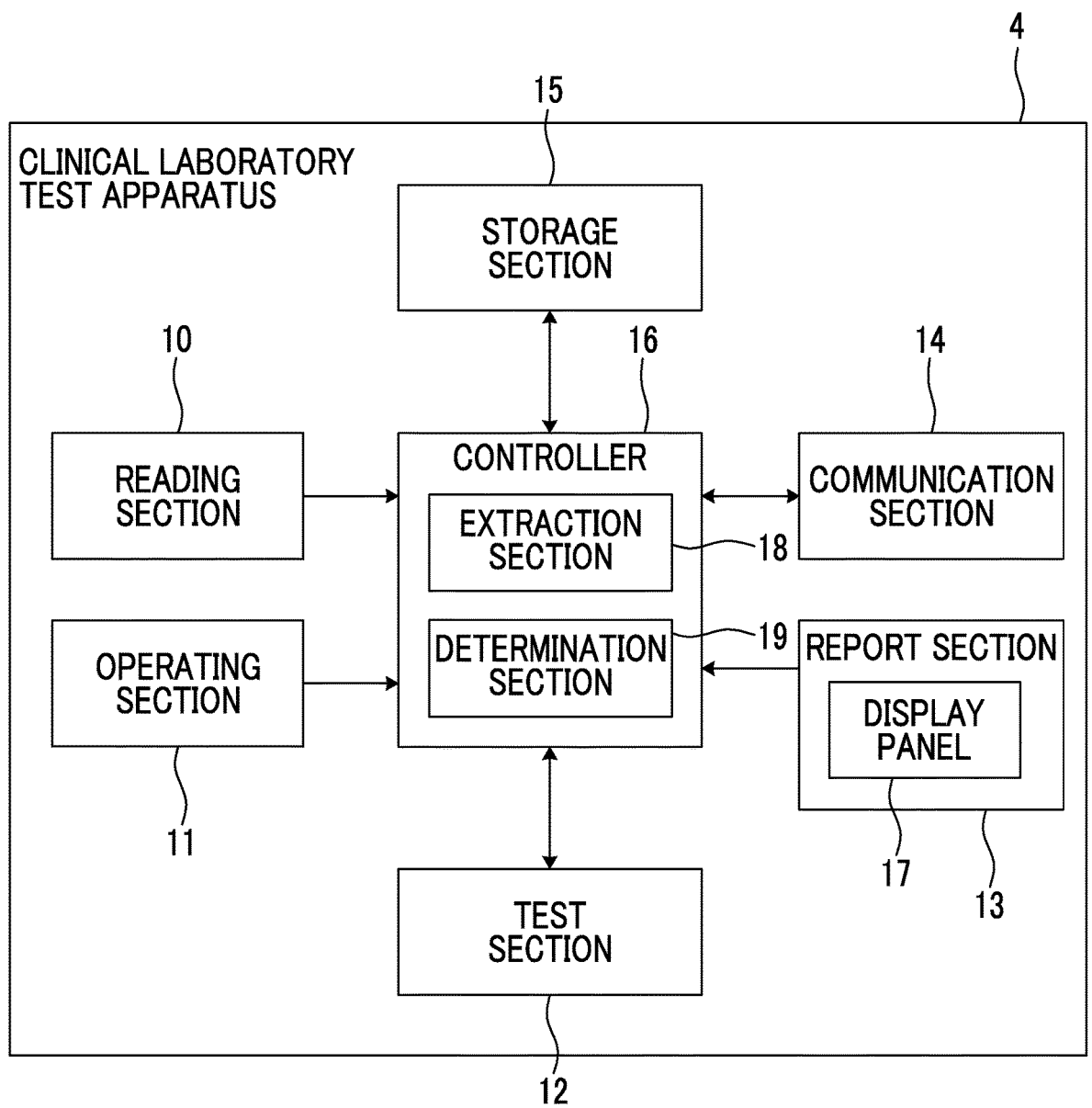
FIG. 2 is a block diagram of an example of a clinical laboratory test apparatus that forms the medical information system in FIG. 1.

FIG. 2 shows a configuration of the clinical laboratory test apparatus 4.

The clinical laboratory test apparatus 4 includes a reading section 10, an operating section 11, a test section 12, a report section 13, a communication section 14, a storage section 15, and a controller 16 that generally controls the reading section 10, the operating section 11, the test section 12, the report section 13, the communication section 14, and the storage section 15.

The reading section 10 reads an optically readable code array. The reading section 10 is appropriately configured according to a configuration of the code array, and in a case where the code array is the above-described one-dimensional code or two-dimensional code, the reading section 10 is configured to include a light emitting element such as a laser diode or a light emitting diode (LED), and a light receiving element such as a photo diode or a charge-coupled device (CCD) image sensor. Here, light that is emitted from the light emitting element to the code array and is reflected from the code array is received by the light receiving element, so that the code array is read on the basis of light intensity distribution based on an array of lines or dots. The code array read by the reading section 10 is input to the controller 16.

The operating section 11 accepts various instructions (for example, a test starting instruction, or the like) from a tester. The operating section 11 is configured by a hardware key such as a switch, for example. An instruction received through the operating section 11 is input to the controller 16.

The test section 12 performs a sample test. The test section 12 is appropriately configured according to a test to be performed. For example, in the immunochromatographic apparatus, the test section 12 includes an imaging section that images a chromatography test piece using an image pickup device such as a CCD image sensor a complementary metal oxide semiconductor (CMOS) image sensor, and an image analysis section that analyzes an image of the test piece acquired by the imaging section. The color presentation of the reaction part shown in the image of the test piece is digitized by the image analysis section, and antigens in the sample liquid are measured. The test result is input to the controller 16.

The report section 13 reports a variety of information to a tester of the clinical laboratory test apparatus 4. The report section 13 includes a display panel 17 such as an LCD, for example, and presents information (for example, a menu, an operating procedure, a test result, or the like) by displaying an image or characters on a display screen of the display panel 17. The display panel 17 may be a so-called touch panel that detects an operation with respect to the display screen, and in this case, the display panel 17 also serves as a part or the entirety of the operating section 11 that receives various instructions of the tester. Further, the report section 13 may include a display light such as an LED, or may report information using a lighting status (turning on, blinking, or turning off). Further, the report section 13 may include a sound generator such as a speaker, or may report information using sound generated from the sound generator.

The communication section 14 is connected to the network 5, and performs reception and transmission of information through the network 5. The communication section 14 is configured by a hardware interface corresponding to a network to be connected.

The storage section 15 stores a program to be executed by the controller 16 and data necessary for execution of the program, and stores a variety of information such as a code array read by the reading section 10 or a test result acquired by the test section 12. The storage section 15 is configured by a memory such as a ROM, a RAM, or an HDD.

The controller 16 is operated according to a program to generally control the operations of the reading section 10, the operating section 11, the test section 12, the report section 13, the communication section 14, and the storage section 15. Further, the controller 16 is operated according to a program to also function as the extraction section 18 and the determination section 19.

The extraction section 18 extracts, from a plurality of code arrays read by the reading section 10, a rule that is common to the plurality of code arrays. Further, the controller 16 stores the extracted rule in the storage section 15. The determination section 19 determines authenticity of the code arrays read by the reading section 10 on the basis of the rule stored in the storage section 15. In addition, the controller 16 operates the test section 12 to execute a test according to the authenticity determination result or to suspend the test execution. The code array rule, the rule extraction method, and the authenticity determination method will be described later in detail.

The program executed by the controller 16 provides two operation modes, that is, a mode (hereinafter, referred to as a rule extraction mode) in which a rule of code arrays is extracted and the extracted rule is stored and a mode (hereinafter, referred to as a test mode) in which the authenticity of the code arrays is determined to perform or suspend a test according to the determination result to the controller 16. The operation modes are selected by an operation with respect to the operating section 11.

A hardware configuration of the controller 16 that executes various processes as the extraction section 18 and the determination section 19 includes a central processing unit (CPU) that is a general-purpose processor, a programmable logic device (PLD) that is a processor having a circuit configuration that is changeable after manufacturing, such as a field programmable gate array (FPGA), an exclusive electric circuit that is a processor having a circuit configuration that is exclusively provided for executing a specific process, such as an application specific integrated circuit (ASIC), or the like.

Each processing section of the extraction section 18 and the determination section 19 may be configured by one processor among the above-mentioned various processors, or may be configured by a combination of the same or different two or more processors (for example, a plurality of FPGAs or a combination of a CPU and an FPGA). Further, a plurality of processing sections may be configured by one processor.

As a first example in which the plurality of processing sections are configured by one processor, there is a configuration in which one processor is configured by a combination of one or more CPUs and software and the processor functions as a plurality of processing sections, as represented by a computer such as a client or a server. As a second example thereof, there is a configuration in which a processor that realizes entire functions of a system that includes a plurality of processing sections by one integrated circuit (IC) chip is used, as represented by a system-on-chip (SoC) or the like. In this way, the plurality of processing sections may be configured using one or more various processors as a hardware structure. Further, the hardware configuration of the various processors specifically refers to an electric circuitry in which circuit elements such as semiconductor elements are combined.

Hereinafter, an operation example of the clinical laboratory test apparatus 4 will be described. In the operation example to be described hereinafter, it is assumed that a code array necessary for execution of a clinical laboratory test that uses the clinical laboratory test apparatus 4 is only a sample code array.

Figure 3:
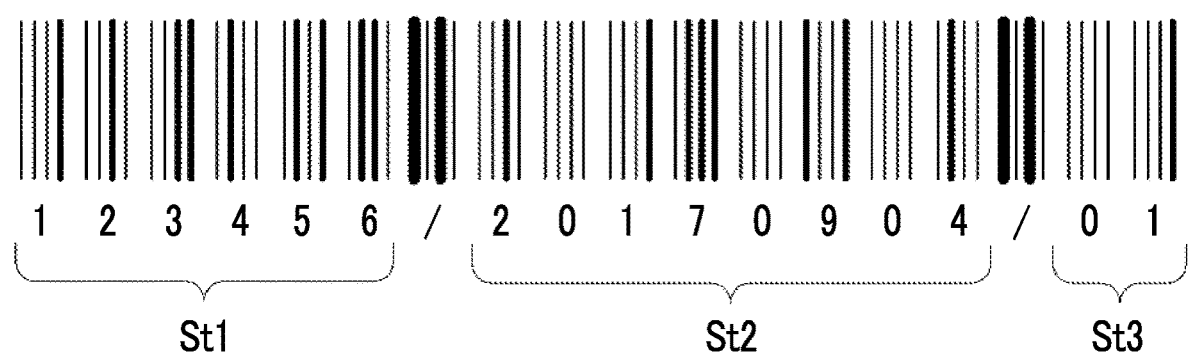
FIG. 3 is a schematic diagram of an example of a code array necessary for execution of a clinical laboratory test using the clinical laboratory test apparatus.

FIG. 3 shows a configuration example of a sample code array.

The sample code array shown in FIG. 3 is the above-mentioned one-dimensional code array. The code array retains a character string St1 indicating a test subject ID, a character string St2 indicating a test date, and a character string St3 indicating a test type as test information. Further, a character string in which the character string St1, the character string St2, and the character string St3 are sequentially arranged, and a predetermined delimiter character "/(slash)" is interposed between the character string St1 and the character string St2, and between the character string St2 and the character string St3 is encoded in accordance with an array pattern of black lines and white lines. The delimiter character is not limited to "/", and may be ". (period)", ", (comma)", ": (colon)", "- (hyphen)", or the like.

The character string St1 indicating the test subject ID is configured on the basis of a predetermined rule. As the rule, the number of characters, the type of characters (numerical characters, alphabets, and signs), or the like may be used. In the shown example, the character string St1 is configured of six numerical characters.

The character string St2 indicating the test date is similarly configured on the basis of a predetermined rule. As the rule, a date format may be used. Using "yyyy" as a year (A.D.) represented by four numerical characters, "yy" as a year (A.D.) represented by two numerical characters, "mm" as a month represented by two numerical characters, and "dd" as a day represented by two numerical characters, the format becomes, for example, "yyyymmdd", "mmddyyyy", "ddmmyyyy", "yymmdd", "mmddyy", or "ddmmyy". Between the year, the month, and the day, a predetermined delimiter character may be inserted. In the shown example, the character string St2 is configured by eight numerical characters in the format of "yyyymmdd".

The character string St3 indicating the test type is similarly configured on the basis of a predetermined rule, and in the shown example, is configured by two numerical characters.

In the sample code array configured as described above, the total number of codes becomes 18. Further, date codes written in the format of "yyyymmdd" are included. Further, the date codes start from the eighth code from the head of the code array, and the seventh code and the sixteenth code from the head of the code array become delimiter character codes corresponding to the delimiter character "/".

The controller 16 of the clinical laboratory test apparatus 4 extracts the above-described rules (the total code number rule, the date code rule, and the delimiter character code rule) of the sample code array using a plurality of sample code arrays, and stores the extracted rules in the storage section 15.

Figure 4:
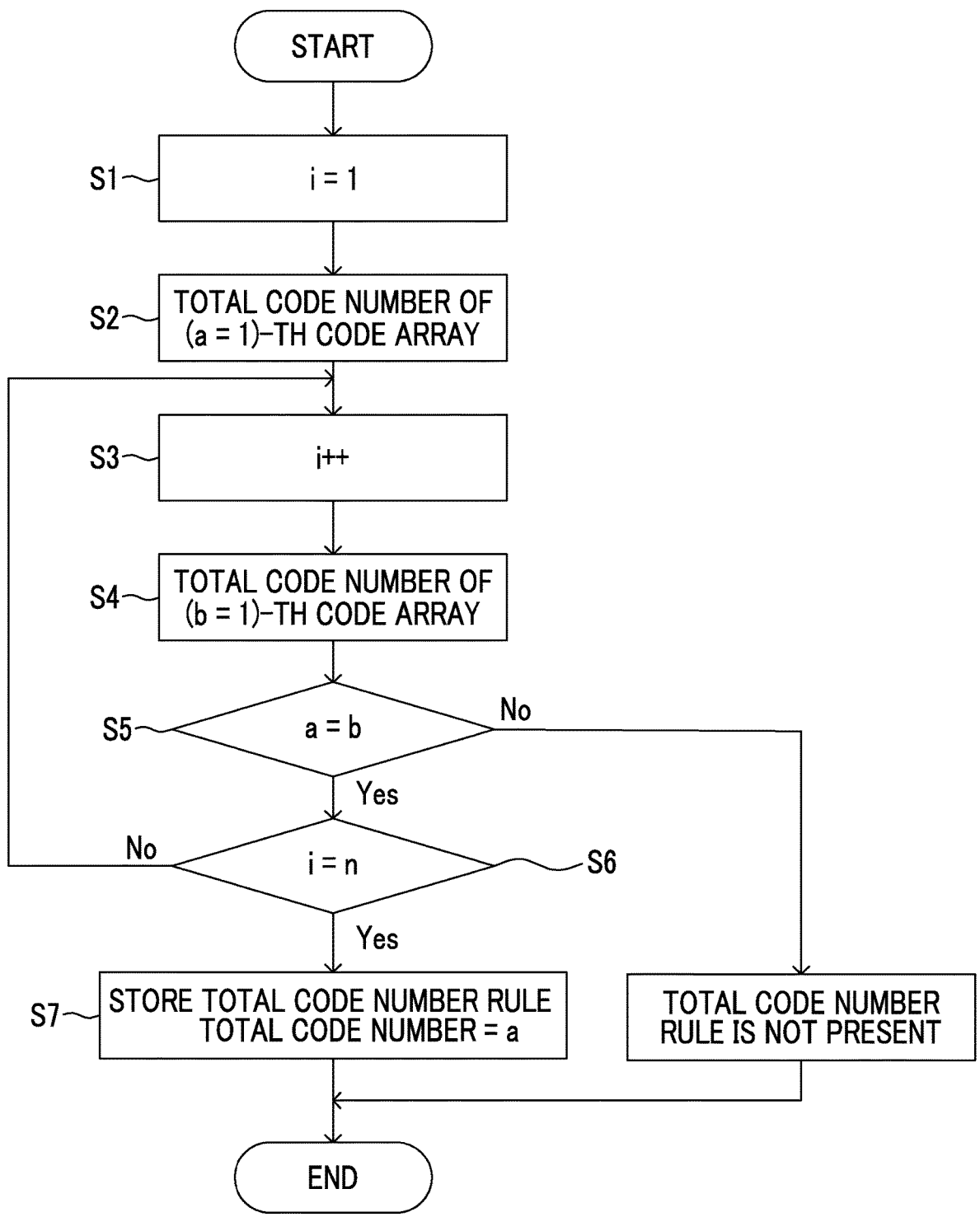
FIG. 4 is a flowchart of an example of an extraction process of a total code number rule, executed by a controller of the clinical laboratory test apparatus.

FIG. 4 shows an example of a process of extracting a total code number rule of a sample code array.

First, it is assumed that the number of code arrays used in extraction of rules of a sample code array is n. Here, n represents an integer that is equal to or greater than 2, which is appropriately set. The operating section 11 of the clinical laboratory test apparatus 4 is operated, and the operation mode of the controller 16 is set to the rule extraction mode. The controller 16 that is set to the rule extraction mode prepares a variable i indicating the number of times of code array reading, and substitutes 1 for the variable i (step S1).

After the initial setting is completed, a message for urging an operator to read a first sample code array is displayed on the display panel 17 of the report section 13, and the first code array is read by the reading section 10. The controller 16 acquires a total code number (a total number of codes) of the read code array, and substitutes the acquired total code number for the variable a (step S2).

Subsequently, the controller 16 increments the variable i (step S3). A message for urging the operator to read an i-th sample code array is displayed on the display panel 17, and the i-th code array is read by the reading section 10. The controller 16 acquires the total code number of the read code array, substitutes the acquired total code number for a variable b (step S4), and compares the variable a with the variable b (step S5).

In a case where the variable a and the variable b do not match each other (No in step S5), the controller 16 stops the extraction of the total code number rule, and determines that there is no total code number rule in the code array used in the rule extraction to then terminate the process. As a case where the variable a and the variable b do not match each other, for example, a case where the i-th code array is contaminated or dust or the like is attached thereto, and thus, the i-th code array is read erroneously, or a case where the i-th code array is a code array different from the sample code array may be considered.

In a case where the variable a and the variable b match each other (Yes in step S5), the controller 16 repeatedly performs the processes from step S3 to step S5 until the variable i that represents the number of times of code array reading reaches n. Further, in a case where the variable i that represents the number of times of code array reading reaches n (Yes in step S6), the controller 16 stores a value of the variable a, that is, a total code number that is common between the first to the n-th code arrays as the total code number rule of the sample code array in the storage section 15 (step S7), and then, normally terminates the process.

In the extraction of the total code number rule, the plurality of code arrays used in the rule extraction may be equal to each other, or may be different from each other.

Figure 5:
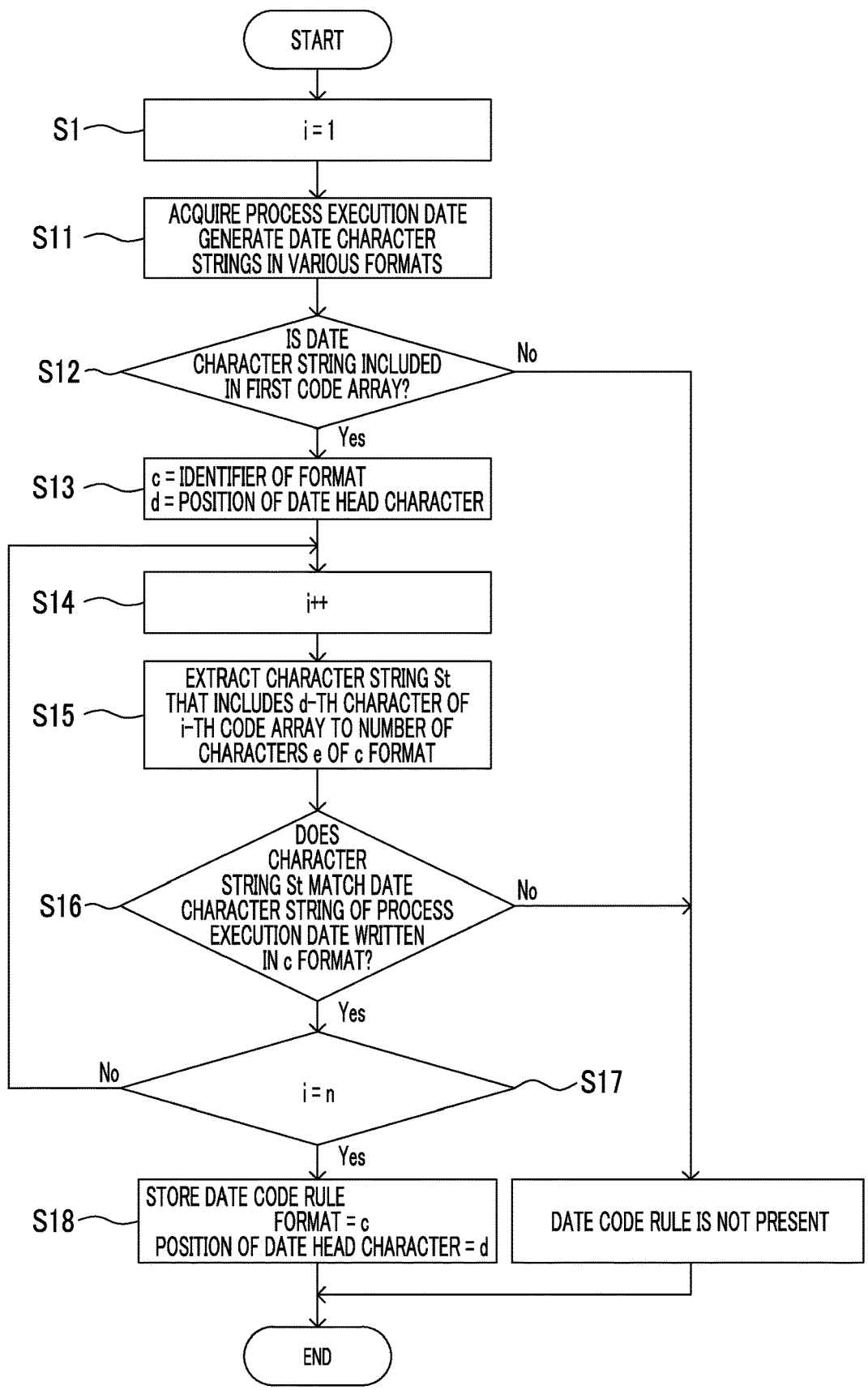
FIG. 5 is a flowchart of an example of an extraction process of a date code rule, executed by the controller of the clinical laboratory test apparatus.

FIG. 5 shows an example of a process of extracting a date code rule.

First, the controller 16 performs the above-described initial setting (step S1). Further, the controller 16 acquires a process execution date, and applies the acquired date to various formats ("yyyymmdd", "mmddyyyy", "ddmmyyyy", "yymmdd", "mmddyy", "ddmmyy", or the like) to generate date character strings written in the various formats (step S11). In a case where the clinical laboratory test apparatus 4 includes a hardware clock, the date may be acquired from the hardware clock. Alternatively, the date may be acquired from the server 2 through the network 5.

After the initial setting is completed, for example, a message for urging an operator to read the first sample code array is displayed on the display panel 17 of the report section 13, and the first code array is read by the reading section 10. Here, it is assumed that the sample code arrays used in the rule extraction are generated on the process execution date and include a date code of the process execution date. The controller 16 performs search for the various date character strings generated in step S11, with respect to the character string indicated by the read code array (step S12).

In a case where any one of the various date character strings generated in step S11 is included in the first code array (No in step S12), the controller 16 stops the extraction of the date code rule, and determines that there is no date code rule in the code array used in the rule extraction to then terminate the process. As a case where any one of the various date character strings is not included in the first code array, for example, a case where the first code array is contaminated, or dust or the like is attached thereto, and thus, the first code array is erroneously read, or a case where the first code array is a code array different from the sample code array may be considered.

In a case where any one of the various data character strings generated in step S11 is included in the first code array (Yes in step S12), the controller 16 substitutes an identifier indicating a type of the format of the date character string included in the first code array for a variable c. Further, the controller 16 substitutes a value indicating which position a head character of the date character string is located at from the head of the code array for a variable d (step S13).

Subsequently, the controller 16 increments the variable i (step S14). A message for urging the operator to read an i-th sample code array is displayed on the display panel 17, and the i-th code array is read by the reading section 10. The controller 16 extracts a character string St that includes the d-th character from the head of the code array to the number of characters e of a format indicated by the identifier c, with respect to character strings expressed by the read code array (step S15). For example, in the case of the format "yyyymmdd", "mmddyyyy" or "ddmmyyyy", e is 8, and in the case of the format "yymmdd", "mmddyy" or "ddmmyy", e is 6.

Further, the controller 16 determines whether or not the character string St extracted in step S15 matches a date character string obtained by writing the process execution date acquired in step S11 in the format indicated by the identifier c (step S16).

In a case where the character string St extracted in step S15 does not match the date character string obtained by writing the process execution date acquired in step S11 in the format indicated by the identifier c (No in step S16), the controller 16 stops the extraction of the date code rule, and determines that there is no date code rule in the code array used in the rule extraction to then terminate the process. As a case where the character string St and the date character string do not match each other, for example, a case where the i-th code array is contaminated, dust or the like is attached, and thus, the i-th code array is read erroneously, or a case where the i-th code array is a code array different from the sample code array may be considered.

In a case where the character string St extracted in step S15 matches the date character string obtained by writing the process execution date acquired in step S11 in the format indicated by the identifier c (Yes in step S16), the controller 16 repeatedly performs the processes from step S14 to step S16 until the variable i that represents the number of times of code array reading reaches n. Further, in a case where the variable i that represents the number of times of code array reading reaches n (Yes in step S17), the controller 16 stores a value of the variable c, that is, a format of a date code that is common between the first to the n-th code arrays, and a value of the variable d, that is, a position in the code array of the date code that is common between the first to the n-th code arrays as the date code rule of the sample code array in the storage section 15 (step S18), and then, normally terminates the process.

In the extraction of the date code rule, the plurality of code arrays used in the rule extraction may be equal to each other, but preferably, are different from each other except for the date code. In a case where the plurality of code arrays are different from each other except for the date code, first, by reading all the plurality of code arrays, and then, extracting a code part that is common between the plurality of read code arrays, it is possible to accurately specify a date code compared with a case where date character strings written in various formats are retrieved.

Figure 6:
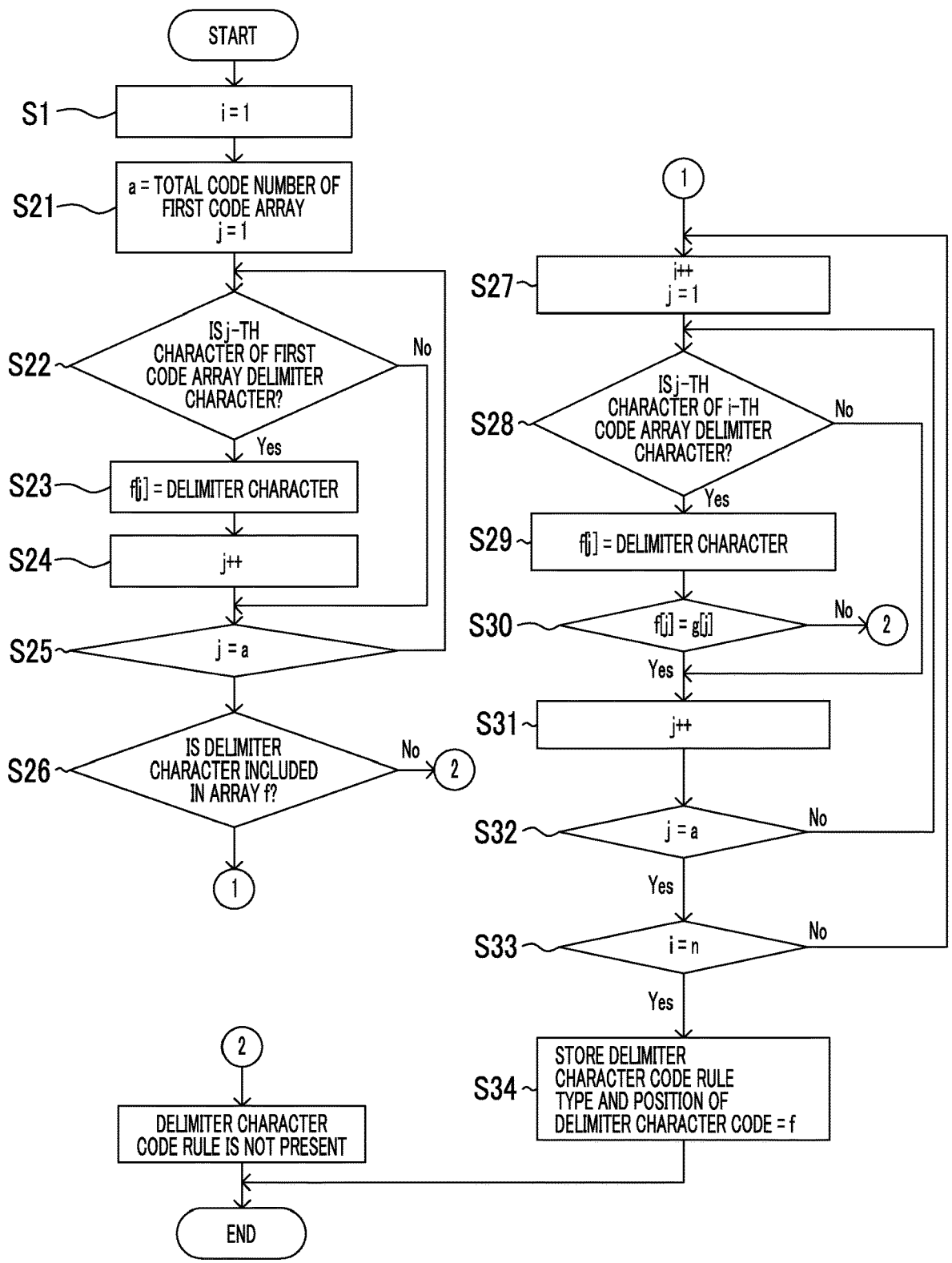
FIG. 6 is a flowchart of an example of an extraction process of a delimiter character code rule, executed by the controller of the clinical laboratory test apparatus.

FIG. 6 shows an example of a process of extracting a delimiter character code rule.

First, the controller 16 performs the above-described initial setting (step S1).

After the initial setting is performed, for example, a message for urging an operator to read the first sample code array is displayed on the display panel 17 of the report section 13, and the first code array is read by the reading section 10. Here, the controller 16 acquires a total code number of the read code arrays, substitutes the read total code number for the variable a, prepares an array f and an array g of the number of elements a, and substitutes 1 for a variable j indicating an element number of the array f and the array g (step S21).

Then, the controller 16 extracts a delimiter character with respect to the first code array. Specifically, the controller 16 determines whether a j-th character from the head of the character string indicated by the first code array corresponds to any one of "/(slash)", ". (period)", ", (comma)", ": (colon)", and "- (hyphen)" (step S22), and only in a case where the determination is affirmative, the controller 16 substitutes the corresponding delimiter character for a j-th element f [j] of the array f (step S23), and increments the variable j (step S24). Until the variable j reaches a (the total code number of the first code array), the controller 16 repeatedly executes the processes from step S22 to step S24 (step S25). Thus, the delimiter character is extracted from the character string indicated by the first code array, and the extracted delimiter character is retained in the array f in a state of being associated with a position in the character string.

Further, the controller 16 determines whether at least one delimiter character is included in the array f (step S26).

In a case where the delimiter character is not included in the array f (No in step S26), the controller 16 stops the extraction of the delimiter character code rule, and determines that there is no delimiter character code rule in the code array used in the rule extraction to then terminate the process. As a case where the delimiter character code is not included in the array f, a case where the first code array is contaminated, dust or the like is attached, and thus, the first code array is erroneously read, or a case where the first code array is a code array different from the sample code array may be considered.

In a case where at least one delimiter character is included in the array f (Yes in step S26), the controller 16 increments the variable i, and substitutes 1 for the variable j (step S27).

Further, a message for urging an operator to read the i-th sample code array is displayed on the display panel 17, and the i-th code array is read by the reading section 10.

The controller 16 performs the delimiter character extraction with respect to the i-th code array. The controller 16 determines whether the j-th character from the head of the character string indicated by the i-th code array corresponds to any one of "/(slash)", ". (period)", ", (comma)", ": (colon)", and "- (hyphen)" (step S28), and only in a case where the determination is affirmative, the controller 16 substitutes the corresponding delimiter character for a j-th element g[j] of the array g (step S29). Further, the controller 16 compares a delimiter character substituted for the element g[j] with a delimiter character substituted for the element f[j] of the array f that retains the delimiter character of the first code array (step S30).

In a case where the element f[j] and the element g[j] do not match each other (No in step S30), the controller 16 stops the extraction of the delimiter character code rule of the sample code array, and determines that there is no delimiter character code rule in the code array used in the rule extraction to then terminate the process. As a case where the element f[j] and the element g[j] do not match each other, a case where the i-th code array is contaminated, dust or the like is attached, and thus, the i-th code array is read erroneously, or a case where the i-th code array is different from the sample code array may be considered.

In a case where the element f[j] and the element g[j] match each other (Yes in step S30), the controller 16 increments the variable j (step S31), and repeatedly performs the processes from step S28 to step S31 until the variable j reaches a (total code number of the first code array) (step S32). Further, the controller 16 repeatedly executes the processes from step S27 to step S32 until the variable i that represents the number of times of code array reading reaches n (step S33). Further, in a case where the variable i that represents the number of times of code array reading reaches n (Yes in step S33), the controller 16 stores the type of a delimiter character code that is common between code arrays from the first code array, that is, the array f, to the n-th code array and a position thereof in the code array as the delimiter character code rule of the sample code array in the storage section 15 (step S34), and then, normally terminates the process.

In the extraction of the delimiter character code rule, n code arrays used in the rule extraction may be equal to each other, or may be different from each other.

FIG. 7 shows an example of a process in a case where a clinical laboratory test is performed. It is assumed that the total code number rule, the date code rule, and the delimiter character code rule are extracted in advance by the controller 16 of the clinical laboratory test apparatus 4 as rules of a sample code array and are stored in the storage section 15. Further, it is assumed that the operation mode of the controller 16 of the clinical laboratory test apparatus 4 is set to a test mode.

A message for urging an operator to read a sample code array is displayed on the display panel 17 of the report section 13, and the sample code array attached to a sample container that contains a sample gathered from a test subject is read by the reading section 10. The controller 16 respectively applies the total code number rule, the date code rule, and the delimiter character code rule of the sample code array with respect to the read code array, and determines authenticity of the read code array on the basis of whether the read code array is suitable for each rule.

First, the controller 16 determines the authenticity on the basis of the total code number rule (step S41). The controller 16 acquires the total code number of the read code array. Further, the controller 16 compares the total code number of the read code array with a total code number stored in the storage section 15 as the total code number rule. In a case where both of them do not match each other, the controller 16 determines that the read code array is not suitable for the total code number rule stored in the storage section 15 (No in step S41), and determines that the read code array is false (step S44).

In a case where the total code number of the read code array and the total code number stored in the storage section 15 as the total code number rule match each other (Yes in step S41), subsequently, the controller 16 determines the authenticity on the basis of the date code rule (step S42).

In the determination of the authenticity based on the date code rule, the controller 16 specifies date codes in the read code array with reference to a format of date codes stored in the storage section 15 as the date code rule and positions of the date codes in the code array. For example, in a case where the format of the date codes stored in the storage section 15 as the date code rule is "yyyymmdd" and a head code of the date codes corresponds to an eighth code from the head of the code array, codes from the eighth code to the fifteenth code are specified as the date codes.

Further, the controller 16 compares a date indicated by the specified date codes in the read code array with a test execution date acquired from a hardware clock provided in the clinical laboratory test apparatus 4 or the server 2. In a case where both of them do not match each other, the controller 16 determines that the read code array is not suitable for the date code rule stored in the storage section 15 (No in step S42), and determines that the read code array is false (step S44).

In a case where the date indicated by the specified date codes in the read code array and the test execution date acquired from the hardware clock provided in the clinical laboratory test apparatus 4 or the server 2 match each other (Yes in step S42), subsequently, the controller 16 determines the authenticity on the basis of the delimiter character code rule (step S43).

In the determination of the authenticity based on the delimiter character code rule, with reference to a position in the code array of a delimiter character code stored in the storage section 15 as the delimiter character code rule, the controller 16 compares a code at the corresponding position in the read code array with the delimiter character code stored in the storage section 15 in association with the position. In a case where both of them do not match each other, the controller 16 determines that the read code array is not suitable for the delimiter character code rule stored in the storage section 15 (No in step S43), and determines that the read code array is false (step S44).

In this way, in a case where the read code array is not suitable for one or more rules among the total code number rule, the date code rule, and the delimiter character code rule, the controller 16 determines that the read code array is false. As a case where it is determined that the code array is false, a case where the read code array is contaminated or dust or the like is attached thereto, and thus, the code array is read erroneously, or a case where the read code array is a code array different from the sample code array may be considered. Further, the controller 16 suspends execution of a clinical laboratory test of a sample in a case where the determination is false.

Preferably, in a case where it is determined that the code array is false, the controller 16 operates the report section 13 to report the determination result of the false determination to the operator of the clinical laboratory test apparatus 4 (step S45). A form of the report is not particularly limited, and for example, the determination result of the false determination may be displayed on the display panel 17. Alternatively, a display light indicating the false determination may be turned on, or a warning sound may be generated from a sound generator such as a speaker. Thus, it is possible to prevent a state where a test is not executed due to the false determination from being left.

On the other hand, in a case where the read code array is suitable for all the rules of the total code number rule, the date code rule, and the delimiter character code rule (Yes in step S43), the controller 16 determines that the read code array is true (step S46), and executes the clinical laboratory test of the sample (step S47). Further, the controller 16 transmits test information retained in the code array determined to be true and the obtained test result to the server 2 in association (step S48).

The test result transmitted to the server 2 from the clinical laboratory test apparatus 4 is stored in the database DB of the server 2, and the test result stored in the database DB is managed by the server 2 in a searchable manner using the test information associated with the test result. Further, a test order corresponding to the transmitted test information is selected by the server 2 from test orders stored in the database DB, a status of the selected test order is changed from non-completion to completion to manage the progress of the test order.

In this way, by causing the clinical laboratory test apparatus 4 to learn (extract and store) an authentic code array rule to be read in execution of a clinical laboratory test, it is possible to determine authenticity of a code array read in the test using only the clinical laboratory test apparatus 4 before execution of the test. Thus, it is possible to prevent or reduce occurrence of inconvenience due to erroneous reading of a code array, such as matching through a manual operation of a test result in a case where the test result is transmitted to the server 2 in a state of being associated with a non-authentic code array (test information) and a test order, or re-testing. Further, it is not necessary to perform bi-directional communication between the clinical laboratory test apparatus 4 and the server 2 for acquisition of a list of test orders stored in the database DB of the server 2, which leads to simplicity of the system 1.

In the above-described example, a configuration where all the rules of the total code number rule, the date code rule, and the delimiter character code rule are used as the sample code array rule has been described, but a configuration in which any one rule among the total code number rule, the date code rule, and the delimiter character code rule is used as the sample code array rule, or a configuration in which a plurality of rules are combined to be used as the sample code array rule may be employed.

Further, a configuration in which a code array necessary for execution of a clinical laboratory test using the clinical laboratory test apparatus 4 is only a sample code array has been described, but a configuration in which a plurality of types of code arrays are necessary therefor may be employed. In a case where the plurality of types of code arrays are necessary, in the rule extraction mode, the rule extraction process shown in FIGS. 4 to 6 may be performed for each type of code array to extract the rules, and the extracted rules may be stored in the storage section 15 for each type of code array. Further, in the test mode, a configuration in which the plurality of types of code arrays are read by the reading section 10 in a predetermined order, authenticity of the read code arrays are sequentially determined on the basis of whether each read code array is suitable for the rules of the type of the corresponding code array, and the test is executed in a case where it is determined that all of the plurality of types of code arrays are true, and the test is suspended in a case where it is determined that one or more types of code arrays among the plurality of types of code arrays are false, may be used.

As the plurality of types of code arrays, a test subject code array, a tester code array, or the like, in addition to the sample code array, may be used. For example, assuming that test subject codes are formed by a character string St1 (see FIG. 3) indicating a test subject ID, as a rule with respect to the test subject codes, the total code number rule may be suitably used. Further, in execution of a clinical laboratory test using the clinical laboratory test apparatus 4, the test subject codes and sample codes are read by the reading section 10, and in a case where it is determined that the test subject codes and the sample codes are all true, the controller 16 determines whether the test subject ID retained in the test subject codes matches a test subject ID included in test information retained in the sample codes, and in a case where both of the test subject IDs match each other, the test is executed, and in a case where both of the test subject IDs do not match each other, the execution of the test is suspended. Thus, it is possible to prevent mix-up of samples.

Further, for example, assuming that tester codes are formed of a character string indicating a tester ID and the character string is formed of a predetermined number of numerical characters similarly to the character string St1 indicating the test subject ID, as a rule with respect to the tester codes, the total code number rule may be suitably used. Further, in execution of a clinical laboratory test using the clinical laboratory test apparatus 4, the tester codes are read by the reading section 10, and in a case where it is determined that the tester codes are true, the controller 16 transmits the tester ID retained in the tester codes and the test result to the server 2 in association. Thus, it is possible to achieve establishment of tradability of the test.

In this way, by using the plurality of types of code arrays, convenience of the system 1 is enhanced.

Processes performed by the controller 16 may be provided as a program for causing a processor to execute these processes. The program may be recorded on a non-transitory processor-readable recording medium to be provided. The "processor-readable recording medium" includes an optical medium such as a compact disc read-only-memory (CD-ROM) or a magnetic recording medium such as a memory card. Further, such a program may be provided by being downloaded through a network.

As described above, a clinical laboratory test apparatus disclosed in the present specification includes a reading section that reads an optically readable code array; an extraction section that extracts, from a plurality of the code arrays read by the reading section, a rule that is common between the plurality of code arrays; a storage section that stores the rule extracted by the extraction section; and a determination section that determines authenticity of each of the code arrays read by the reading section on the basis of the rule stored in the storage section. The rule includes a total code number of the code array, and the determination section determines that the code array is true in a case where the total code number of the code array read by the reading section matches a total code number of the rule, and determines that the code array is false in a case where the total code number of the code array read by the reading section does not match the total code number of the rule. In testing a sample, in a case where it is determined by the determination section that the code array read by the reading section is true, the test is executed, and in a case where it is determined that the code array is false, the execution of the test is suspended.

Further, a clinical laboratory test apparatus disclosed in the present specification includes a reading section that reads an optically readable code array; an extraction section that extracts, from a plurality of the code arrays read by the reading section, a rule that is common between the plurality of code arrays; a storage section that stores the rule extracted by the extraction section; and a determination section that determines authenticity of each of the code arrays read by the reading section on the basis of the rule stored in the storage section. The rule includes a format of date codes included in the code array and positions thereof in the code array, and the determination section determines that the code array is true in a case where the format and the positions of the date codes of the code array read by the reading section match a format and positions of date codes of the rule, and determines that the code array is false in a case where the format and the positions of the date codes of the code array read by the reading section do not match the format and the positions of the date codes of the rule. In testing a sample, in a case where it is determined by the determination section that the code array read by the reading section is true, the test is executed, and in a case where it is determined that the code array is false, the execution of the test is suspended.

Further, in the clinical laboratory test apparatus disclosed in the present specification, the plurality of code arrays from which the rule is extracted are different from each other except for the date codes.

Further, a clinical laboratory test apparatus disclosed in the present specification includes a reading section that reads an optically readable code array; an extraction section that extracts, from a plurality of the code arrays read by the reading section, a rule that is common between the plurality of code arrays; a storage section that stores the rule extracted by the extraction section; and a determination section that determines authenticity of each of the code arrays read by the reading section on the basis of the rule stored in the storage section. The rule includes a type of a delimiter character code included in the code array and a position thereof in the code array, and the determination section determines that the code array is true in a case where the type and the position of the delimiter character code of the code array read by the reading section match a type and a position of a delimiter character code of the rule, and determines that the code array is false in a case where the type and the position of the delimiter character code of the code array read by the reading section do not match the type and the position of the delimiter character code of the rule. In testing a sample, in a case where it is determined by the determination section that the code array read by the reading section is true, the test is executed, and in a case where it is determined that the code array is false, the execution of the test is suspended.

Further, in the clinical laboratory test apparatus disclosed in the present specification, a plurality of types of code arrays are necessary for the execution of the test, and the storage section stores the rule for each type of the code array.

Further, the clinical laboratory test apparatus disclosed in the present specification further includes a report section that reports a determination result of the determination section.

Further, a system disclosed in the present specification includes a server that manages a test order and a test result; and the clinical laboratory test apparatus, in which the code array determined to be true by the determination section includes a code array that retains test information for specifying the test order, and the clinical laboratory test apparatus transmits the code array determined to be true by the determination section in testing a sample and a test result obtained by the test to the server in association.

What is claimed is:

1. A clinical laboratory test apparatus comprising:
a reading section that reads an optically readable code array;
an extraction section that extracts, from a plurality of the code arrays read by the reading section, a rule that is common between the plurality of code arrays;
a storage section that stores the rule extracted by the extraction section; and
a determination section that determines authenticity of each of the code arrays read by the reading section based on the rule stored in the storage section,
wherein the rule comprises a total code number of the code array,
wherein the determination section determines that the code array is true in a case where a total code number of the code array read by the reading section matches the total code number of the rule, and determines that the code array is false in a case where the total code number of the code array read by the reading section does not match the total code number of the rule, and
wherein in testing a sample, in a case where the code array read by the reading section is determined by the determination section to be true, the test is executed, and in a case where the code array read by the reading section is determined by the determination section to be false, the execution of the test is suspended.

2. A clinical laboratory test apparatus comprising:
a reading section that reads an optically readable code array;
an extraction section that extracts, from a plurality of the code arrays read by the reading section, a rule that is common between the plurality of code arrays;
a storage section that stores the rule extracted by the extraction section; and
a determination section that determines authenticity of each of the code arrays read by the reading section based on the rule stored in the storage section,
wherein the rule comprises a format of date codes included in the code array and positions of the date codes in the code array,
wherein the determination section determines that the code array is true in a case where a format and positions of the date codes of the code array read by the reading section match the format and the positions of the date codes of the rule, and determines that the code array is false in a case where the format and the positions of the date codes of the code array read by the reading section do not match the format and the positions of the date codes of the rule, and
wherein in testing a sample, in a case where the code array read by the reading section is determined by the determination section to be true, the test is executed, and in a case where the code array read by the reading section is determined by the determination section to be false, the execution of the test is suspended.

3. The clinical laboratory test apparatus according to claim 2,
wherein the plurality of code arrays from which the rule is extracted are different from each other except for the date codes.

4. A clinical laboratory test apparatus comprising:
a reading section that reads an optically readable code array;
an extraction section that extracts, from a plurality of the code arrays read by the reading section, a rule that is common between the plurality of code arrays;
a storage section that stores the rule extracted by the extraction section; and
a determination section that determines authenticity of each of the code arrays read by the reading section based on the rule stored in the storage section,
wherein the rule comprises a type of a delimiter character code included in the code array and a position of the delimiter character code in the code array,
wherein the determination section determines that the code array is true in a case where a type and a position of the delimiter character code of the code array read by the reading section match the type and the position of the delimiter character code of the rule, and determines that the code array is false in a case where the type and the position of the delimiter character code of the code array read by the reading section do not match the type and the position of the delimiter character code of the rule, and
wherein in testing a sample, in a case where the code array read by the reading section is determined by the determination section to be true, the test is executed, and in a case where the code array read by the reading section is determined by the determination section to be false, the execution of the test is suspended.

5. The clinical laboratory test apparatus according to claim 1,
wherein a plurality of types of code arrays are necessary for the execution of the test, and
wherein the storage section stores the rule for each of the types of the code arrays.

6. The clinical laboratory test apparatus according to claim 2,
wherein a plurality of types of code arrays are necessary for the execution of the test, and
wherein the storage section stores the rule for each of the types of the code arrays.

7. The clinical laboratory test apparatus according to claim 3,
wherein a plurality of types of code arrays are necessary for the execution of the test, and
wherein the storage section stores the rule for each of the types of the code arrays.

8. The clinical laboratory test apparatus according to claim 4,
wherein a plurality of types of code arrays are necessary for the execution of the test, and
wherein the storage section stores the rule for each of the types of the code arrays.

9. The clinical laboratory test apparatus according to claim 1, further comprising:
a report section that reports a result of the determining of the determination section.

10. The clinical laboratory test apparatus according to claim 2, further comprising:
a report section that reports a result of the determining of the determination section.

11. The clinical laboratory test apparatus according to claim 3, further comprising:

a report section that reports a result of the determining of the determination section.

12. The clinical laboratory test apparatus according to claim 4, further comprising:
a report section that reports a result of the determining of the determination section.

13. The clinical laboratory test apparatus according to claim 5, further comprising:
a report section that reports a result of the determining of the determination section.

14. The clinical laboratory test apparatus according to claim 6, further comprising:
a report section that reports a result of the determining of the determination section.

15. The clinical laboratory test apparatus according to claim 7, further comprising:
a report section that reports a result of the determining of the determination section.

16. The clinical laboratory test apparatus according to claim 8, further comprising:
a report section that reports a result of the determining of the determination section.

17. A system comprising:
a server that manages a test order and a test result; and
the clinical laboratory test apparatus according to claim 1,
wherein the code array determined to be true by the determination section comprises a code array that retains test information for specifying the test order, and
wherein the clinical laboratory test apparatus transmits the code array determined to be true by the determination section in testing a sample and a test result obtained by the test to the server in association with each other.

18. A system comprising:
a server that manages a test order and a test result; and
the clinical laboratory test apparatus according to claim 2,
wherein the code array determined to be true by the determination section comprises a code array that retains test information for specifying the test order, and
wherein the clinical laboratory test apparatus transmits the code array determined to be true by the determination section in testing a sample and a test result obtained by the test to the server in association with each other.

19. A system comprising:
a server that manages a test order and a test result; and
the clinical laboratory test apparatus according to claim 4,
wherein the code array determined to be true by the determination section comprises a code array that retains test information for specifying the test order, and
wherein the clinical laboratory test apparatus transmits the code array determined to be true by the determination section in testing a sample and a test result obtained by the test to the server in association with each other.

* * * * *